(12) United States Patent
Aoki et al.

(10) Patent No.: US 6,787,561 B1
(45) Date of Patent: Sep. 7, 2004

(54) BENZIMIDAZOLE COMPOUNDS

(75) Inventors: Kozo Aoki, Minami-ashigara (JP); Kazuhiro Aikawa, Minami-ashigara (JP); Masayuki Kawakami, Minami-ashigara (JP); Yongzhe Yan, Hiratsuka (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/019,668

(22) PCT Filed: Jul. 7, 2000

(86) PCT No.: PCT/JP00/04531

§ 371 (c)(1),
(2), (4) Date: Jun. 5, 2002

(87) PCT Pub. No.: WO01/04110

PCT Pub. Date: Jan. 18, 2001

(30) Foreign Application Priority Data

Jul. 7, 1999 (JP) ............................................. 11-193356
Sep. 14, 1999 (JP) ........................................... 11-260384

(51) Int. Cl.$^7$ ................ A61K 31/4439; A61K 31/4178; C07D 401/12; C07D 403/12
(52) U.S. Cl. ....................... 514/338; 514/387; 514/242; 514/255.05; 514/274; 514/312; 514/367; 514/369; 514/375; 514/381; 548/305.4; 548/251; 548/181; 548/159; 548/221; 546/273.7; 546/157; 544/405; 544/298; 544/182
(58) Field of Search ................... 548/305.4; 546/273.7; 514/338, 387

(56) References Cited

U.S. PATENT DOCUMENTS 4,329,347 A * 5/1982 Muller et al. ................ 514/256
4,971,980 A 11/1990 Giani et al.

FOREIGN PATENT DOCUMENTS

EP 583665 A2 2/1994
EP 0 849 259 A1 6/1998
EP 0 987 254 A1 3/2000
EP 1 201 664 A1 5/2002
GB 1250531 A * 10/1971
WO WO 95/34304 A1 12/1995
WO WO 97/03970 A1 2/1997
WO WO 98/54153 A1 12/1998
WO WO 99/25712 A1 5/1999

OTHER PUBLICATIONS

Journal of Medicinal Chemistry, 35, (23), 4384–92, 1992.
Tracy F. Gregory, et al. "Parallel Synthesis of a Series of Subtype–Selective NMDA Receptor Antagonists", Boorganic & Medicinal Chemistry Letters, vol. 10, 2000, pp. 527–529.

* cited by examiner

*Primary Examiner*—Laura L. Stockton
(74) *Attorney, Agent, or Firm*—Sughrue Mion, PLLC

(57) ABSTRACT

A benzimidazole compound or a salt thereof which has an inhibitory action of forming of macrophages and is useful as an active ingredient of an orally available medicament for preventive and/or therapeutic treatment of arteriosclerosis, which is represented by the formula (I):

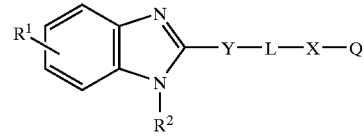

wherein, $R^1$ represents one or more functional groups on the benzene ring selected from the group consisting of hydrogen atom, a halogen atom, a lower alkyl group and a lower alkoxy group; $R^2$ represents hydrogen atom, an alkyl group or an acyl group; L represents a $C_4$–$C_8$ alkylene group or an ethyleneoxy linking group represented as $(CH_2CH_2O)_n CH_2CH_2$ wherein n represents 1 or 2; X represents O or NH; Y represents S or a single bond; and Q represents a 5- or 6-membered heterocyclic group which may have a functional group on the ring.

14 Claims, No Drawings

BENZIMIDAZOLE COMPOUNDS

TECHNICAL FIELD

The present invention relates to benzimidazole compounds useful as active ingredients of medicaments.

BACKGROUND ART

In recent years, patients with so-called adult diseases such as arterial sclerosis, hypertension, and diabetes mellitus have been continuously increasing with prolongation of life expectancy. In particular, patients with hyperlipidemia and arterial sclerosis derived therefrom have been remarkably increasing due to excessive intake of high calorie and high cholesterol food, which have become a serious social problem. Medications currently applied for treatment of hyperlipidemia and arterial sclerosis are those symptomatically lower cholesterol in blood, and no medicament that can be expected to have potency in retracting arterial sclerosis lesions has been used clinically. Arterial sclerosis is characterized by lesions of intimal hyperplasia and lipid accumulation in blood vessels, and it has been elucidated from recent biochemical findings that foaming of macrophages plays a main role in the formation of arterial sclerosis lesions. Accordingly, suppression of the foaming of macrophages may possibly prevent arterial sclerosis by inhibiting formation of arterial sclerosis lesions, or achieve radicular treatment of arterial sclerosis by retraction of arterial sclerosis lesions. However, no medicament having such activity has been known.

It has been suggested that an inhibitor of ACAT, an enzyme involved in intestinal absorption and metabolism of cholesterol, such as imidazole derivatives described in Bio. Med. Chem. Lett., Vol. 5(2), 167–172 (1995) reduces blood cholesterol level and thus suppresses the foaming of macrophages in an animal experiment (for example, piperazine derivatives described in International Publication WO98/54153). However, since these compounds are directed to ACAT inhibitory activity, they do not achieve satisfactory inhibition of the foaming of macrophages, and their effects are insufficient.

Some amide compounds are reported to have ACAT inhibitory action (for example, the amide compounds disclosed in International Publication WO99/25712). However, ACAT inhibitors have recently been recognized to have various toxicities and side effects (for example, Toxycol. Pharmacol., 22, 510–518 (1994); Toxicol. Appl. Pharmacol., 140, 387–392 (1996)). It is considered that medicaments for treatment of arteriosclerosis, which are required to be administered for a long period of time, advantageously have no ACAT inhibitory action with such side effects.

Some benzimidazole compounds are suggested to suppress the foaming of macrophages (for example, the imidazole compounds disclosed in EP849259). However, the compounds are not satisfactory in suppression of the foaming of macrophages and they fail to exert potent effect in vivo because their uptakes into animal bodies are very poor. As medicaments for treatment of arteriosclerosis or hyperlipidemia are taken by patients for a long period of time at home, the medicaments are required to be developed as oral preparations. Therefore, it is essential that these medicaments give a high value of AUC (area under the plasma concentration) that relates to uptake into living bodies through oral administration. However, the conventional imidazole compounds have a problem of poor oral absorbability.

DISCLOSURE OF THE INVENTION

An object of the present invention is to provide a compound having activity of suppressing the foaming of macrophages, and is useful as an active ingredient of a medicament for preventive and/or therapeutic treatment of arterial sclerosis. Another object of the present invention is to provide a compound having the aforementioned activity, and is useful as an active ingredient of medicament for preventive and/or therapeutic treatment of hyperlipidemia. In particular, the object of the present invention is to provide a compound that can achieve the desired therapeutic effect by oral administration.

The inventors of the present invention conducted various researches to achieve the foregoing objects, and as a result, they found that novel benzimidazole compounds represented by the formula (I) set out below have activity of suppressing the foaming of macrophages, and are useful as active ingredients of preventive and/or therapeutic medicament of arterial sclerosis and preventive and/or therapeutic medicament of hyperlipidemia. They also found that these compounds can readily be uptaken into living bodies and exert superior therapeutic effect by oral administration. The present invention was achieved on the basis of these findings.

The present invention thus provides benzimidazole compounds represented by the following formula (I):

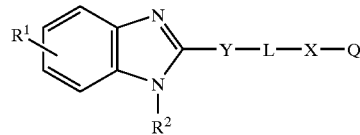

[in the formula, $R^1$ represents one or more functional groups on the benzene ring selected from the group consisting of hydrogen atom, a halogen atom, a lower alkyl group, and a lower alkoxy group; $R^2$ represents hydrogen atom, an alkyl group, or an acyl group; L represents a $C_4$–$C_8$ alkylene group or an ethyleneoxy linking group represented by $(CH_2CH_2O)_nCH_2CH_2$ (in the formula, n represents 1 or 2); X represents O or NH (NH may have a functional group on the nitrogen atom); Y represents S or a single bond; and Q represents a 5- or 6-membered heterocyclic group which may have a functional group on the ring (the heterocyclic group may have a condensed ring)] and salts thereof.

According to preferred embodiments of the present invention, provided are the aforementioned compounds and salts thereof, wherein Y is S; the aforementioned compounds and salts thereof, wherein $R^1$ and $R_2$ represent hydrogen atom; the aforementioned compounds and salts thereof, wherein L is a $C_4$–$C_8$ alkylene group; the aforementioned compounds and salts thereof, wherein Q is a residue of a heterocyclic ring selected from the group consisting of pyridine, pyrimidine, pyrazine, triazine, quinoline, pyrrole, thiophene, furan, imidazole, pyrazole, triazole, tetrazole, thiazole, thiadiazole, oxazole, oxadiazole, benzimidazole, benzoxazole, and benzothiazole; the aforementioned compounds and salts thereof, wherein X is O; and the aforementioned compounds and salts thereof, wherein Q is a residue of a heterocyclic ring selected from the group consisting of pyridine, thiazole, benzimidazole, benzoxazole and benzothiazole.

As other aspects of the present invention, provided are methods for preparing the compounds represented by the aforementioned formula (I), and medicaments comprising a compound represented by the aforementioned formula (I) or a physiologically acceptable salt thereof as an active ingredient. As preferred embodiments of the aforementioned medicaments, pharmaceutical compositions are provided which comprise the aforementioned compounds or a physiologically acceptable salt thereof as an active ingredient and an additive for pharmaceutical preparation. The medicaments of the present invention are useful as, for example, those for preventive and/or therapeutic treatment of hyperlipidemia and for preventive and/or therapeutic treatment of arteriosclerosis. The medicaments are also useful as agents for suppressing foaming of macrophages, agents for retracting arterial sclerosis lesions, and agents for inhibiting formation of arteriosclerotic lesion.

As further aspects of the present invention, provided are uses of the compounds represented by the aforementioned formula (I) or salts thereof for manufacture of the aforementioned medicaments, and methods for preventive and/or therapeutic treatment of hyperlipidemia and methods for preventive and/or therapeutic treatment of arteriosclerosis, which comprise the step of administering a preventively and/or therapeutically effective amount of the compound represented by the aforementioned formula (I) or a physiologically acceptable salt thereof to a mammal including human.

BEST MODE FOR CARRYING OUT THE INVENTION

In the specification, a lower alkyl group or a lower alkyl moiety of a functional group that contains the lower alkyl moiety (e.g., lower alkoxy group) may be a linear, branched or cyclic alkyl group, or a combination thereof. For example, an alkyl group having 1–4 carbon atoms (for example, methyl group, ethyl group, n-propyl group, isopropyl group, n-butyl group, sec-butyl group, tert-butyl group and the like) may be used. A halogen atom referred to in the specification may be any of fluorine atom, chlorine atom, bromine atom and iodine atom.

An alkyl group or an alkyl moiety of a functional group that contains the alkyl moiety (e.g., an alkoxy group, an alkanoyl group, an alkylthio group and the like) referred to in the specification may be linear, branched or cyclic alkyl group, or a combination thereof. An example includes an alkyl group having 1–8 carbon atoms (e.g., methyl group, ethyl group, butyl group, octyl group and the like), and a preferred example includes an alkyl group having 14 carbon atoms (e.g., methyl group, ethyl group, n-propyl group, n-butyl group). An aryl group or an aryl moiety of a functional group that contains the aryl moiety (arylcarbonyl group and the like) is preferably a monocyclic or bicyclic aryl group having a 6- to 10-membered ring, and more specifically, phenyl group, naphthyl group and the like can be used. An alkyl group or an alkyl moiety of a functional group having the alkyl moiety, a lower alkyl group or a lower alkyl moiety of the functional group having the lower alkyl moiety, or an aryl group may have one or two functional groups at any positions. When two or more functional groups exist, they may be the same or different.

Examples of the acyl group include an alkanoyl group, an arylcarbonyl group, an alkylsulfonyl group, an arylsulfonyl group, an alkoxycarbonyl group, a sulfamoyl group, a carbamoyl group and the like. Examples of the alkanoyl group include an alkanoyl group having 1–8 carbon atoms (e.g., acetyl group, butanoyl group, octanoyl group and the like), preferably an alkanoyl group having 1–4 carbon atoms (e.g., acetyl group, butanoyl group and the like). Examples of the arylcarbonyl group include an arylcarbonyl group having 6–10 carbon atoms (e.g., benzoyl group, naphthoyl group and the like). Examples of the alkoxycarbonyl group include an alkoxycarbonyl group having 1–8 carbon atoms (e.g., methoxycarbonyl group, ethoxycarbonyl group, octyloxycarbonyl group and the like), preferably an alkoxycarbonyl group having 1–4 carbon atoms (e.g., methoxycarbonyl group, ethoxycarbonyl group and the like).

Examples of the alkylsulfonyl group include an alkylsulfonyl group having 1–8 carbon atoms (e.g., methanesulfonyl group, butanesulfonyl group, octanesulfonyl group and the like) and examples of the arylsulfonyl group include an arylsulfonyl group having 6–10 carbon atoms (e.g., benzenesulfonyl group, naphthalenesulfonyl group and the like). Examples of the sulfamoyl group include a sulfamoyl group having 0–8 carbon atoms (e.g., sulfamoyl group, methylsulfamoyl group, diethylsulfamoyl group, octylsulfamoyl group, hexadecylsulfamoyl group, phenylsulfamoyl group and the like), preferably a sulfamoyl group having 0–4 carbon atoms (e.g., sulfamoyl group, methylsulfamoyl group, diethylsulfamoyl group and the like). Examples of the carbamoyl group include a carbamoyl group having 0–8 carbon atoms (e.g., carbamoyl group, methylcarbamoyl group, diethylcarbamoyl group, octylcarbamoyl group, hexadecylcarbamoyl group, phenylcarbamoyl group and the like), preferably a carbamoyl group having 0–4 carbon atoms (e.g., methylcarbamoyl group, diethylcarbamoyl group and the like). The aforementioned acyl group may have on or more functional groups at any position. When two or more functional groups exist, they may be the same or different.

$R^1$ represents one or more functional groups on the benzene ring selected from the group consisting of hydrogen atom, a halogen atom, a lower alkyl group, and a lower alkoxy group. When $R^1$ represents two or more functional groups, they may be the same or different, and substitution positions on the benzene ring are not also particularly limited. The halogen atom represented by $R^1$ may preferably be fluorine atom, chlorine atom, or bromine atom. $R^1$ may preferably be hydrogen atom, methyl group, methoxy group, or chlorine atom, and more preferably hydrogen atom.

$R^2$ is preferably hydrogen atom, a $C_1$–$C_4$ alkyl group, or a $C_1$–$C_4$ alkanoyl group, and most preferably hydrogen atom. L represents a linking group, and more specifically a $C_4$–$C_8$ alkylene group (e.g., butylene group, pentamethylene group, hexamethylene group, octamethylene group and the like) or an ethyleneoxy linking group represented by $(CH_2CH_2O)_nCH_2CH_2$ (in the formula, n represents 1 or 2). These linking groups may be linear or branched. The linking group represented by L is preferably a $C_5$–$C_8$ alkylene group (pentamethylene group, hexamethylene group, heptamethylene group, octamethylene group and the like) or the aforementioned ethyleneoxy bridging group, and most preferably a $C_5$–$C_6$ alkylene group. Y is preferably S. X is preferably O or NH, and NH may have a functional group on the nitrogen atom. Although kind of the functional group is not particularly limited, for example, a $C_1$–$C_4$ alkyl group, a $C_1$–$C_4$ alkanoyl group and so forth can be used. X is preferably O.

Q represents a 5- or 6-membered heterocyclic group which contains one or more hetero atoms selected from the group consisting of a nitrogen atom, a sulfur atom and an oxygen atom. The heterocyclic ring may be saturated or partially saturated, or an aromatic heterocyclic ring. Further, the heterocyclic ring may be condensed with a benzene ring or another heterocyclic ring. The heterocyclic group may have one or more functional groups on the ring. Examples of the functional group include a halogen atom, an alkyl group, an aryl group, a heterocyclic group, nitro group, an amino group, an acylamino group, a sulfonamide group, an alkoxycarbonyl group, a carbamoyl group, an alkoxy group, an aryloxy group, hydroxy group, an alkylthio group, an arylthio group, mercapto group, cyano group, oxo group, thioxo group, and oxide on a nitrogen atom or a sulfur atom and so forth.

Examples of the heterocyclic ring constituting the heterocyclic group represent by Q include, for example, pyridine (e.g., 2-pyridyl, 4-pyridyl group), pyrimidine (e.g., 2-pyrimidyl, 3-pyrimidyl group), pyrazine (e.g., 2-pyrazyl group), triazine (e.g., 1,2,4-triazyl group), quinoline (e.g., 2-quinolyl, 4-quinolyl, 8-quinolyl group), pyrrole (e.g., 2-pyrrolo group), thiophene (e.g., 2-thienyl group), furan (e.g., 2-furyl group), imidazole (e.g., 2-imidazolyl group), pyrazole (e.g., 3-pyrazolyl group), triazole (e.g., 1,2,4-triazo-3-yl group), tetrazole (e.g., 1,2,3,4-tetrazo-5-yl group), thiazole (e.g., 2-thiazolyl group, 3-isothiazolyl group, 5-isothiazolyl group), thiadiazole (e.g., 2-thiadiazolyl group), oxazole (e.g., 2-oxazolyl group, 3-isooxazolyl group), oxadiazole (e.g., 2-oxadiazolyl group), benzimidazole (e.g., 2-benzimidazolyl), benzoxazole (e.g., 2-benzoxazolyl), benzothiazole (2-benzothiazolyl) and the like. Q is preferably a 5- or 6-membered heterocyclic group containing one or more nitrogen atoms (which may have a condensed ring). The heterocyclic ring that constitutes the heterocyclic group is most preferably pyridine, thiazole, benzimidazole, benzoxazole or benzothiazole.

Preferred compounds according to the present invention will be exemplified below. However, the scope of the present invention is not limited to these examples.

| No. | k | R¹ | R² | X | Q |
|-----|---|-----|-----|---|---|
| 1 | 5 | H | H | O | 2-pyridyl |
| 2 | 5 | H | H | O | 1-phenyl-tetrazol-5-yl |
| 3 | 5 | H | H | O | 2-quinolyl |
| 4 | 5 | H | H | O | 2-pyrazyl |
| 5 | 5 | H | H | O | 2-thiazolyl |
| 6 | 5 | H | H | O | 2-pyrimidyl |
| 7 | 5 | H | H | O | 2-benzothiazolyl |
| 8 | 5 | H | H | O | 2-benzoxazolyl |
| 9 | 5 | H | H | O | 1-methyl-2-benzimidazolyl |
| 10 | 8 | H | H | O | 2-pyridyl |
| 11 | 4 | H | H | O | 2-pyridyl |
| 12 | 6 | H | H | O | 2-pyridyl |
| 13 | 7 | H | H | O | 2-pyridyl |
| 14 | 5 | H | Cl | O | 2-pyridyl |
| 15 | 5 | 5,6-Cl₂ | H | O | 2-pyridyl |
| 16 | 5 | 5-CH₃ | H | O | 2-pyridyl |
| 17 | 5 | 5-OCH₃ | H | O | 2-pyridyl |
| 18 | 5 | 5-AcNH | H | O | 2-pyridyl |

Structural formula:

R¹—[benzimidazole]—S—(CH₂)ₖ—X—Q with R² on N

-continued

| No. | | R¹ | R² | X | Q |
|---|---|---|---|---|---|
| 19 | 5 | H | H | O | 4-pyridyl |
| 20 | 5 | H | H | O | 1-(prop-1-en-2-yl)-2-benzimidazolyl |
| 21 | 5 | H | H | O | 1H-2-benzimidazolyl |
| 23 | 5 | H | CH$_3$ | O | 2-pyridyl |
| 24 | 5 | H | COC$_2$H$_5$ | O | 2-pyridyl |
| 25 | 6 | H | H | O | 4-pyridyl |
| 26 | 8 | H | H | O | 4-pyridyl |
| 27 | 4 | H | H | O | 4-pyridyl |
| 28 | 5 | H | CH$_2$OCH$_3$ | NH | pyrazinyl |
| 29 | 5 | H | H | NH | 1,2,4-triazinyl |
| 30 | 5 | H | H | NH | 2-benzothiazolyl |
| 31 | 5 | H | H | NH | 2-benzoxazolyl |
| 32 | 6 | H | H | NH | 2-benzoxazolyl |
| 33 | 5 | 5-Cl | H | NH | 2-benzoxazolyl |
| 34 | 5 | 5-CH$_3$ | H | NH | 2-benzoxazolyl |

$$R^1\text{---benzimidazole}\text{---}S\text{---}(CH_2CH_2O)_n\text{---}CH_2CH_2\text{---}X\text{---}Q$$

| No. | R¹ | R² | n | X | Q |
|---|---|---|---|---|---|
| 35 | H | H | 1 | NH | 2-benzoxazolyl |
| 36 | H | H | 2 | NH | 2-benzoxazolyl |

$$R^1\text{---benzimidazole}\text{---}S\text{---}(CH_2)_k\text{---}X\text{---}Q$$

| No. | k | R¹ | R² | X | Q |
|---|---|---|---|---|---|
| 22 | 6 | H | H | O | 2-pyridyl |

The compounds of the present invention represented by the aforementioned formulas (I) may form acid addition salts, and such acid addition salts fall within the scope of the present invention. Examples of the acid addition salts include, for example, mineral acid salts such as hydrochlorides, hydrobromides, nitrates, sulfates, and phosphates, and organic acid salts such as p-toluenesulfonates, methanesulfonates, oxalates, tartrates, malates, and citrates. Further, depending on the type of a functional group, they may also form base addition salts. Furthermore, the compounds of the present invention and salts thereof may exist as hydrates or solvates. Any of the compounds in free forms or in the forms of salts, and hydrates and solvates thereof falls within the scope of the present invention.

The compounds of the present invention may have one or more asymmetric carbons depending on the kind of a functional group. In such compounds, steroisomers such as optical isomers based on one or more asymmetric carbons and diastereoisomers based on two or more asymmetric carbons may exist. Any of stereoisomers in pure forms, any mixtures of the stereoisomers, racemates and the like fall within the scope of the present invention.

The compounds of the present invention can be prepared from readily available raw material compounds by methods well known to those skilled in the art, for example, in accordance with the following scheme. Specific procedures of these methods are explained in detail in the examples of the specification, and those skilled in the art can easily produce the compounds of the present invention by referring to the general explanations given below and the examples, and by adding suitable alterations or modifications to these methods as required (the symbols used in the scheme have the same meanings as those defined above).

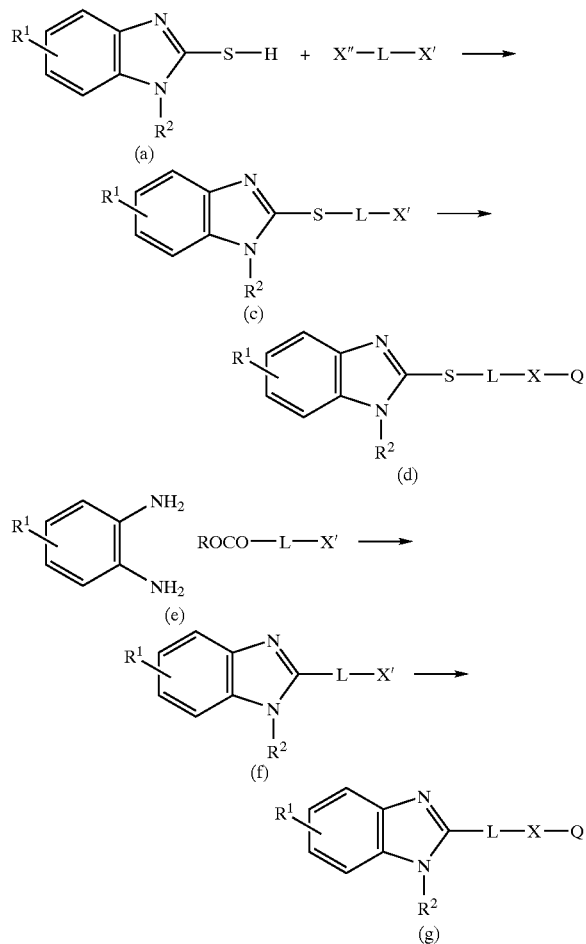

Where Y is S and X is O, a 2-mercaptobenzimidazole derivative (a) and a halide alcohol (b) having a linking chain (L) (as the halide, chloride, bromide, iodide or the like can be used, and a sulfonate such as tosylate or methanesulfonate may also be used instead of the halide; specific examples thereof include 5-bromo-1-pentanol and the like) are reacted to obtain a compound (c) (X'=O). As a solvent, alcohols, acetonitrile and the like can be used, and reaction temperature may be from room temperature to 150° C., preferably about 50° C. to 120° C. Further, when a base such as triethylamine is used as an acid scavenger, the reaction may sometimes progress faster, thereby the reaction temperature may be lowered and the reaction time may be shortened. The compound (c) can be reacted with a halide of heterocyclic ring (e.g., 2-chloropyridine and the like) under an alkaline condition to obtain a compound (d) (X=O). The reaction can be carried out by using a caustic alkali in a solvent such as dimethyl sulfoxide (DMSO), and the reaction temperature is about 100° C. to 160° C. Where a crown ether or the like is used for the reaction, the reaction may sometimes be markedly promoted.

Further, opposite to the aforementioned steps, a compound (d) can also be produced by reacting a halide of heterocyclic ring (e.g., 2-chloropyridine and the like) with a diol compound having a linking group (L) (e.g., 1,5-pentanediol) to produce an alcohol compound in which one of hydroxyl groups is replaced with a heterocyclyloxy group, and then converting the alcohol into a sulfonate in a conventional manner, and further reacting the sulfonate with 2-mercaptobenzimidazole. The reaction of the halide of heterocyclic ring and the diol compound can be preferably performed by using metallic sodium, potassium t-butoxide, sodium methylate or the like as a base catalyst at about −20° C. to 100° C., preferably 0° C. to 50° C., in a solvent such as tetrahydrofuran (THF), dimethylacetamide (DMAc), DMSO or the like. As the sulfonate, tosylate or methanesulfonate can be used. The reaction of the sulfonate and 2-mercaptobenzimidazole can be performed in a solvent such as alcohols and acetonitrile at room temperature to 150° C., preferably about 50° C. to 120° C. When a base such as triethylamine is used as an acid scavenger, the reaction may sometimes progress faster, thereby the reaction temperature may be lowered and the reaction time may be shortened.

Where Y is S and X is NH, a 2-mercaptobenzimidazole derivative (a) and a compound (b) having a linking chain (L) (bi-functional halogeno compound such as chloride, bromide or iodide, sulfonate compound such as tosylate or methanesulfonate or the like, more specifically, dibromopentane, bis-2-chloroethyl ether or the like) are reacted to obtain a compound (c) in which one of functional groups is replaced with the 2-mercaptobenzimidazole derivative. As a solvent, alcohols, acetonitrile and the like can be used, and reaction temperature may be from room temperature to 150° C., preferably about 50° C. to 120° C. Further, when a base such as triethylamine is used as an acid scavenger, the reaction may sometimes progress faster, thereby the reaction temperature may be lowered and the reaction time may be shortened.

The compound (b) wherein only one of the functional groups is a halide or sulfonate is subjected to the reaction (the remaining functional group may optionally be hydroxyl group, acetate moiety or the like, and the reaction condition for said compound may be the same as that mentioned above), and then the resulting compound (c) is subjected to substitution of X' with a halide or sulfonate. For example, substitution from hydroxyl group to a halide or sulfonate can be conducted by a conventional method utilizing tosyl chloride, carbon tetrabromide/triphenylphosphine or the like. NH group of the compound (c) as a halide or sulfonate is protected with a silyl group, methoxymethyl group or the like, and then the product is reacted with an aminoheterocyclic ring, and the protective group can be removed to obtain a compound (d) (X=NH). This reaction can be performed by using a base catalyst, preferably sodium hydride, and dimethylformamide (DMF), DMAc, DMSO, dimethyl-imidazolinone or the like as a solvent at 0° C. to 50° C.

As another route, a compound (c) (X'=halogen) can be reacted with potassium phthalimide and immediately hydrolyzed by using hydrazine hydrate to obtain an amino compound (c) (X'=NH$_2$). The amino compound can be reacted with a halide of heterocyclic ring (e.g., 2-chlorobenzothiazole and the like) to obtain a compound (d) (X=NH).

Where Y is a single bond, a target compound (g) can be obtained by cyclizing o-phenylenediamine (e) and a hydroxyalkylcarboxylic acid or an ester thereof by condensation under an acidic condition to form a benzimidazole ring to produce a compound (f), and then reacting the resulting product with a halide of heterocyclic ring under an alkaline condition in the same manner as mentioned above. The reaction of o-phenylenediamine (e) and the hydroxyalkylcarboxylic acid or an ester compound thereof can be performed by heating them to 120° C. to 150° C. in aqueous hydrochloric acid.

The compounds of the present invention have a potent activity of suppressing the foaming of macrophages which is involved in the formation of arterial sclerosis lesions in arterial sclerosis. Therefore, the compounds are useful as an active ingredient of a medicament for preventive and/or therapeutic treatment of arterial sclerosis, and an active ingredient of a medicament for preventive and/or therapeutic treatment of hyperlipidemia by lowering blood cholesterol. Although it is not intended to be bound by any specific theory, it has been known that invasion of foamed macrophages into arterial walls triggers hyperplasia of smooth muscles of arterial walls, thereby causing arterial sclerosis (Schaffner, T. et al., Amer. J. Pathol., 110, pp.57–73, 1980; Gerrity, R. G., Amer. J. Pathol. 103, pp.181–190, 1981). The medicaments of the present invention directly inhibit the formation of arterial sclerosis lesions and enables retraction of arterial sclerosis lesions by suppressing the foaming of macrophages which is involved in the formation of arterial sclerosis lesions. Accordingly, the medicaments of the present invention are useful for prevention and/or treatment of arterial sclerosis and hyperlipidemia brought by various causes.

As the active ingredients of the medicaments of the present invention, a substance selected from the group consisting of the compounds represented by the aforementioned formula (I) and salts thereof, and hydrates thereof and solvates thereof can be used. Routes of administration of the aforementioned medicament are not particularly limited, and they can be administered orally or parenterally. Oral administration is preferred. Although the aforementioned substance as the active ingredient, per se, may be used as the medicament of the present invention, it is generally desirable to provide the medicament as a pharmaceutical composition in a form well known to those skilled in the art by adding pharmaceutical additives as required.

Examples of the pharmaceutical composition suitable for oral administration include, for example, tablets, capsules, powders, subtilized granules, granules, solutions, syrups and the like. Examples of the pharmaceutical composition suitable for parenteral administration include, for example, injections, fusion drips, suppositories, inhalants, transdermal preparations, transmucosal preparations, patches and the like. As the pharmaceutical additives, excipients, disintegrating agents or dissolving aids, isotonic agents, pH modifiers, stabilizers, propellants, tackifiers and the like can be used, and they can optionally be used in combination.

For example, for the manufacture of the pharmaceutical composition suitable for oral administration, transdermal administration, or transmucosal administration, usable pharmaceutical additives include excipients such as glucose, lactose, D-mannitol, starch and crystalline cellulose; excipients or disintegrating aids such as carboxymethyl cellulose, starch and carboxymethyl cellulose calcium; binders such as hydroxypropyl cellulose, hydroxypropylmethyl cellulose, polyvinylpyrrolidone and gelatin; lubricants such as magnesium stearate and talc; coating agents such as hydroxypropylmethyl cellulose, sucrose, polyethylene glycol and titanium oxide; bases such as vaseline, liquid paraffin, polyethylene glycol, gelatin, kaoline, glycerol, purified water and hard fat and the like. Further, the pharmaceutical composition can also be produced by using pharmaceutical additives such as, for example, propellants such as frons, diethyl ether and compressed gases; tackifiers such as sodium polyacrylate, polyvinyl alcohol, methyl cellulose, polyisobutylene and polybutene; base fabrics such as cotton cloth, and plastic sheets and the like.

For preparation of the pharmaceutical composition suitable for injection or drip infusion, usable pharmaceutical additives include, for example, dissolving agents and dissolving aids that can form aqueous injections or injections that are dissolved upon use such as distilled water for injection, physiological saline and propylene glycol; isotonic agents such as glucose, sodium chloride, D-mannitol and glycerol; pH modifiers such as inorganic salts, organic acids, inorganic bases and organic bases and the like.

Doses of the medicament of the present invention are not particularly limited, and suitably chosen depending on dosage forms, purpose of administration, i.e., preventive and/or therapeutic purpose, the age, body weight, and symptoms of a patient and the like. For example, for intravenous administration, about 10 mg to 400 mg per day for an adult as the amount of an active ingredient can be administered, and for oral administration, about 10 mg to 800 mg per day for an adult as the amount of an active ingredient can be administered. Preferred doses for an adult are 10 mg to 100 mg per day and 10 mg to 300 mg per day, respectively, as the amount of an active ingredient. The medicament of the present invention may be administered once or several times a day, and any administration period may be applied depending on the age of a patient and improvement of symptoms and the like.

EXAMPLE

The present invention will be explained more specifically with reference to the following examples. However, the scope of the present invention is not limited to the following examples. The compound numbers in the examples correspond to the compound numbers in the table mentioned above.

Example 1
Synthesis of 2-(5-(1-phenyltetrazolyl-5-oxy)pentylthio) benzimidazole (Compound 2)

Example 1a
Synthesis of 5-(5-hydroxypentyloxy)-1-phenyltetrazole 10 ml of THF solution containing 225 mg of potassium t-butoxide was added with 0.6 g of 1,5-pentanediol and 0.36 g of 5-chloro-1-phenyl-tetrazole and the mixture was stirred at room temperature for 2 hours. The reaction mixture was added with water and extracted with ethyl acetate. The extract was dried over sodium sulfate, and the solvent was evaporated under reduced pressure. The resulting residue was purified by silica gel column chromatography (ethyl acetate:hexane) to obtain 0.4 g of the title compound (yield: 81%).

Example 1b
Synthesis of 5-(5-tosyloxypentyloxy)-1-phenyltetrazole 0.5 g of pyridine and 0.31 g of p-toluenesulfonyl chloride were added to a solution of 0.4 g of the compound obtained in Example 1a in dichloromethane (10 ml) and the mixture was stirred for 6 hours. The organic layer was washed with 10% aqueous citric acid and then with water and dried over sodium sulfate. The solvent was evaporated under reduced pressure and the resulting residue was purified by silica gel column chromatography (ethyl acetate:hexane) to obtain 0.35 g of the title compound (yield: 54%).

Example 1c
Synthesis of 2-(5-(1-phenyltetrazolyl-5-oxy)pentylthio)benzimidazole 0.35 g of the compound obtained in Example 1b and 0.14 g of 2-mercaptobenzimidazole were refluxed in 10 ml of acetonitrile containing 0.1 g of triethylamine for 4 hours. The reaction mixture was cooled to room temperature, then added with water and extracted with ethyl acetate. The extract was dried over sodium sulfate. The solvent was evaporated under reduced pressure, and the resulting residue was purified by silica gel column chromatography (ethyl acetate:hexane) to obtain 0.2 g of the title compound (yield: 60%).

$^1$H-NMR (CDCl$_3$) (ppm): 1.65 (m, 2H), 1.89 (m, 4H), 3.35 (t, 2H), 4.62 (t, 2H), 7.20 (m, 2H), 7.42–7.58 (m, 5H), 7.70 (m, 2H)

MS (FAB$^+$): m/z 381 (MH$^+$)

The following compounds were synthesized in the same manner as in Example 1.

2-(5-Hydroxypentyloxy)quinoline, yield: 68%
2-(5-Tosyloxypentyloxy)quinoline, yield: 61%
(Compound 3) Purified by silica gel column chromatography (ethyl acetate:hexane), yield: 42%.
$^1$H-NMR (CDCl$_3$) (ppm): 1.66 (m, 2H), 1.88 (m, 4H), 3.38 (t, 2H), 4.46 (t, 2H), 6.88 (d, 2H), 7.20 (m, 4H), 7.38 (m, 2H), 7.62 (m, 2H), 7.73 (dd, 2H), 7.84 (d, 2H), 7.98 (d, 2H)
MS (FAB$^+$): m/z 364 (MH$^+$) 2-(5-Hydroxypentyloxy)pyrazine, yield: 55%
2-(5-Tosyloxypentyloxy)pyrazine, yield; 70%
(Compound 4) Purified by silica gel column chromatography (ethyl acetate:hexane), yield: 55%.
$^1$H-NMR (CDCl$_3$) (ppm): 1.65 (m, 2H), 1.85 (m, 4H), 3.38 (t, 2H), 4.30 (t, 2H), 7.21 (m, 2H), 7.53 (m, 2H), 8.09 (dd, 2H), 8.21 (d, 2H)
MS (FAB$^+$): m/z 315 (MH$^+$)
2-(5-Hydroxypentyloxy)thiazole, yield: 80%
2-(5-Tosyloxypentyloxy)thiazole, yield: 66%
(Compound 5) Purified by silica gel column chromatography (ethyl acetate:hexane), yield: 47%.
$^1$H-NMR (CDCl$_3$) (ppm): 1.60 (m, 2H), 1.82 (m, 4H), 3.34 (t, 2H), 4.37 (t, 2H), 6.69 (d, 1H), 7.15 (d, 1H), 7.21 (m, 2H), 7.52(m, 2H)
MS (FAB$^+$): m/z 320 (MH$^+$)
2-(5-Hydroxypentyloxy)pyrimidine, yield: 64%
2-(5-Tosyloxypentyloxy)pyrimidine, yield: 56%
(Compound 6) Purified by silica gel column chromatography (ethyl acetate:hexane), yield: 48%.
$^1$H-NMR (CDCl$_3$) (ppm): 1.61 (m, 2H), 1.82 (m, 4H), 3.32 (t, 2H), 4.36 (t, 2H), 6.95 (t, 1H), 7.21 (m, 2H), 7.51 (br, 2H), 8.54 (dd, 2H)
MS (FAB$^+$): m/z 315 (MH$^+$)
2-(5-Hydroxypentyloxy)benzothiazole, yield: 69%
2-(5-Tosyloxypentyloxy)benzothiazole, yield: 74%
(Compound 7) Purified by silica gel column chromatography (ethyl acetate:hexane), yield: 53%.
$^1$H-NMR (CDCl$_3$) (ppm): 1.61 (m, 2H), 1.83 (m, 4H), 3.34 (t, 2H), 4.51 (t, 2H), 7.19 (m, 3H), 7.34 (tm, 1H), 7.49 (m, 2H), 7.64 (t, 2H)
MS (FAB$^+$): m/z 370 (MH$^+$)
2-(5-Hydroxypentyloxy)benzoxazole, yield: 66%
2-(5-Tosyloxypentyloxy)benzoxazole, yield: 59%
(Compound 8) Purified by silica gel column chromatography (ethyl acetate:hexane), yield: 47%.
$^1$H-NMR (CDCl$_3$) (ppm): 1.63 (m, 2H), 1.87 (m, 4H), 3.34 (t, 2H), 4.52 (t, 2H), 7.14 (m, 4H), 7.29 (m, 1H), 7.46(m, 3H)
MS (FAB$^+$): m/z 352 (M–H)

Example 2
Synthesis of 2-(5-(2-benzimidazolylthio)pentyloxy-1-methylbenzimidazole (Compound 9)

Example 2a
Synthesis of 2-(5-hydroxypentyloxy)-1-methylbenzimidazole (Compound 9)

1.2 g 1,5-pentadiol and 0.1 g of sodium were stirred for 30 minutes with heating under nitrogen atmosphere. After the sodium disappeared, the reaction mixture was added dropwise with 0.6 g of 2-chloro-1-methylbenzimidazole dissolved in 10 ml of anhydrous THF and refluxed for 8 hours. The reaction mixture was cooled to room temperature, then added with water and extracted with ethyl acetate. The extract was dried over anhydrous sodium sulfate, and the solvent was evaporated under reduced pressure. The resulting residue was purified by silica gel column chromatography (carrier: silica gel, developing solvent: ethyl acetate:hexane) to obtain 0.6 g of the title compound (yield: 71%).

Example 2b
Synthesis of 2-(5-tosyloxypentyloxy)-1-methylbenzimidazole

The title compound was obtained in the same manner as in Example 1b (yield: 36%).

Example 2c
Synthesis of 2-(5-(2-benzimidazolylthio)pentyloxy-1-methylbenzimidazole (Compound 9)

The title compound was obtained in the same manner as in Example 1c (yield: 70%).

$^1$H-NMR (CDCl$_3$) (ppm): 1.60 (m, 2H), 1.87 (m, 4H), 3.34 (t, 2H), 3.56 (s, 3H), 4.55 (t, 2H), 7.19 (m, 5H), 7.62 (m, 3H)

MS (FAB$^+$): m/z 367 (MH$^+$)

Example 3
Synthesis of 5-chloro-2-(5-(2-pyridyloxy)pentylthio)benzimidazole (Compound 14)

Example 3a
Synthesis of 2-(5-hydroxypentyloxy)pyridine 10.5 g of 1,5-pentadiol, 5.68 g of 2-chloropyridine, 5.6 g of KOH and 5.3 g of 18-crown-6-ether were added to 20 ml of toluene and the mixture was refluxed for 8 hours. After cooling, the reaction mixture was added with water and extracted with chloroform. The extract was dried over sodium sulfate, and the solvent was evaporated under reduced pressure. The resulting residue was purified by silica gel column chromatography (ethyl acetate:hexane) to obtain 6.5 g of the title compound (yield: 72%).

Example 3b
Synthesis of 2-(5-tosyloxy-pentyloxy)pyridine 5 ml of pyridine and 7 g of p-toluenesulfonyl chloride were added to a solution of 6.5 g of the compound obtained in Example 3a in 20 ml of dichloromethane and then the mixture was stirred for 4 hours. The organic layer was washed with 10% aqueous citric acid and then with water and dried over sodium sulfate. The solvent was evaporated under reduced pressure, and the resulting residue was purified by silica gel column chromatography (ethyl acetate) to obtain 6.57 g of the title compound (yield: 53%).

Example 3c
5-Chloro-2-(5-(2-pyridyloxy)pentylthio)benzimidazole (Compound 14)

0.67 g of the compound obtained in Example 3b and 0.37 g of 5-chloro-2-mercaptobenzimidazole were refluxed for 5 hours in 15 ml of acetonitrile containing 0.25 g of triethylamine. The reaction mixture was cooled to room temperature, then added with water and extracted with ethyl acetate. The extract was dried over sodium sulfate and the solvent was evaporated under reduced pressure. The resulting residue was purified by silica gel column chromatography (ethyl acetate:hexane) to obtain 0.25 g of the title compound (yield: 42%).
$^1$H-NMR (CDCl$_3$) (ppm): 1.58 (m, 2H), 1.80 (m, 4H), 3.31 (t, 2H), 4.24 (t, 2H), 6.73 (d, 1H), 6.88 (t, 1H), 7.15 (dd, 1H), 7.38 (d, 2H), 7.49 (s, 1H), 7.59 (t, 1H), 8.15 (dd, 1H)
MS (FAB$^+$): m/z 348 (MH$^+$)

Example 4
Synthesis of 5,6-dichloro-2-(5-(2-pyridyloxy)pentylthio) benzimidazole (Compound 15)

The title compound was obtained in the same manner as in as Example 3c by using the compound obtained in Example 3b and 5,6-dichloro-2-mercapto-benzimidazole (yield: 44%).
FB 71047
$^1$H-NMR (CDCl$_3$) (ppm): 1.63 (m, 2H), 1.84 (m, 4H), 3.33 (t, 2H), 4.27 (t, 2H), 6.74 (dd, 1H), 6.89 (t, 1H), 7.59 (m, 3H), 8.17 (dd, 1H)
MS (FAB$^+$): m/z 382 (MH$^+$)

Example 5
Synthesis of 5-methyl-2-(5-(2-pyridyloxy)pentylthio) benzimidazole (Compound 16)

The title compound was obtained in the same manner as in Example 3c (yield: 49%) by using the compound obtained in Example 3b and 5-methyl-2-mercapto-benzimidazole.
$^1$H-NMR (CDCl$_3$) (ppm): 1.56 (m, 2H), 1.80 (m, 4H), 2.43 (s, 3H), 3.30 (t, 2H), 4.24 (t, 2H), 6.71 (d, 1H), 6.87 (t, 1H), 7.02 (dd, 1H), 7.29 (s, 1H), 7.41 (d, 1H), 7.57 (t, 1H), 8.16 (dd, 1H)
MS (FAB$^+$): m/z 328 (MH$^+$)

Example 6
Synthesis of 5-methoxy-2-(5-(2-pyridyloxy)pentylthio) benzimidazole (Compound 17)

The title compound was obtained in the same manner as in Example 3c (yield: 58%) by using the compound obtained in Example 3b and 5-methoxy-2-mercapto-benzimidazole.
$^1$H-NMR (CDCl$_3$) (ppm): 1.58 (m, 2H), 1.80 (m, 4H), 3.29 (t, 2H), 3.80 (s, 3H), 4.24 (t, 2H), 6.71 (d, 1H), 6.85 (m, 2H), 7.05 (s, 1H), 7.40 (d, 1H), 7.57 (t, 1H), 8.15 (dd, 1H)
MS (FAB$^-$): m/z 342 (M–H)

Example 7
Synthesis of 5-acetylamino-2-(5-(2-pyridyloxy)pentylthio) benzimidazole (Compound 18)

The title compound was obtained in the same manner as in Example 3c (yield: 48%) by using the compound obtained in Example 3b and 5-acetylamino-2-mercapto-benzimidazole.
$^1$H-NMR (CDCl$_3$) (ppm): 1.61 (m, 2H), 1.80 (m, 4H), 2.15 (s, 3H), 3.31 (t, 2H), 4.26 (t, 2H), 6.71 (d, 1H), 6.84 (t, 1H), 7.12 (d, 1H), 7.42 (d, 1H), 7.55 (t, 1H), 7.99 (s, 1H), 8.12 (dd, 1H), 9.17 (s, 1H)
MS (FAB$^+$): m/z 371 (MH$^+$)

Example 8
Synthesis of 2-(5-(2-pyridyloxy)pentylthio)benzimidazole (Compound 1)

The title compound was obtained in the same manner as in Example 3c (yield: 64%) by using the compound obtained in Example 3b and 2-mercaptobenzimidazole.
$^1$H-NMR (CDCl$_3$) (ppm): 1.66 (m, 2H), 1.87 (m, 4H), 3.38 (t, 2H), 4.30 (t, 2H), 6.73 (d, 1H), 6.88 (dd, 1H), 7.22 (m, 2H), 7.52 (br, 2H), 7.59 (dd, 1H), 8.17 (dd, 1H), 9.67 (br, 1H)
MS (FAB$^+$): m/z 314 (MH$^+$)

Example 9
Synthesis of 2-(4-(2-pyridyloxy)butylthio)benzimidazole (Compound 11)

Example 9a
2-(4-Hydroxybutyloxy)pyridine

The title compound was obtained in the same manner as in Example 3a (yield: 80%) by using 1,4-butanediol and 2-chloropyridine.

Example 9b
2-(4-Tosyloxybutyloxy)pyridine

The title compound was obtained in the same manner as in Example 3b (yield: 51%) from the compound obtained in Example 9a.

Example 9c
2-(4-(2-Pyridyloxy)butylthio)benzimidazole (Compound 11)

The title compound was obtained in the same method as Example 3c (yield: 64%) by using the compound obtained in Example 9b and 2-mercaptobenzimidazole.
$^1$H-NMR (CDCl$_3$) (ppm): 1.94 (m, 4H), 3.40 (t, 2H), 4.30 (t, 2H), 6.71 (d, 1H), 6.87 (t, 1H), 7.19 (m, 2H), 7.50–7.58 (m, 3H), 8.16 (dd, 1H)
MS (FAB$^-$): m/z 298 (M–H)

Example 10
Synthesis of 2-(6-(2-pyridyloxy)hexylthio)benzimidazole (Compound 12)

Example 10a
2-(6-Hydroxyhexyloxy)pyridine

The title compound was obtained in the same manner as in Example 3a (yield: 72%) by using 1,6-hexadiol and 2-chloropyridine.

Example 10b
2-(6-Tosyloxyhexyloxy)pyridine

The title compound was obtained in the same manner as in Example 3b (yield: 50%) from the compound obtained in Example 10a.

Example 10c
2-(6-(2-Pyridyloxy)hexylthio)benzimidazole (Compound 12)

The title compound was obtained in the same manner as in Example 3c (yield: 50%) by using the compound obtained in Example 10b and 2-mercaptobenzimidazole.
$^1$H-NMR (CDCl$_3$) (ppm): 1.46 (m, 4H), 1.77 (m, 4H), 3.33 (t, 2H), 4.26 (t, 2H), 6.73 (d, 1H), 6.87 (t, 1H), 7.19 (m, 2H), 7.51–7.58 (m, 3H), 8.17 (dd, 1H)
MS (FAB$^-$): m/z 326 (MH$^-$)

Example 11
Synthesis of 2-(7-(2-pyridyloxy)heptylthio)benzimidazole (Compound 13)

Example 11a
2-(7-Hydroxyheptyloxy)pyridine

The title compound was obtained in the same manner as in Example 3a (yield: 75%) by using 1,7-heptadiol and 2-chloropyridine.

Example 11b
2-(7-Tosyloxyheptyloxy)pyridine

The title compound was obtained in the same manner as in Example 3b (yield: 49%) from the compound obtained in Example 11a.

Example 11c
2-(7-(2-Pyridyloxy)heptylthio)benzimidazole (Compound 13)

The title compound was obtained in the same manner as in Example 3c (yield: 54%) by using the compound obtained in Example 11b and 2-mercaptobenzimidazole.

$^1$H-NMR (CDCl$_3$) (ppm): 1.38 (m, 6H), 1.75 (m, 4H), 3.32 (t, 2H), 4.26 (t, 2H), 6.74 (d, 1H), 6.87 (t, 1H), 7.20 (m, 2H), 7.51–7.58 (m, 3H), 8.17 (dd, 1H)

MS (FAB$^-$): m/z 340 (M–H)

Example 12
Synthesis of 2-(8-(2-pyridyloxy)octylthio)benzimidazole (Compound 10)

Example 12a
2-(8-Hydroxyoctyloxy)pyridine

The title compound was obtained in the same manner as in Example 3a (yield: 76%) by using 1,8-octadiol and 2-chloropyridine.

Example 12b
2-(8-Tosyloxyoctyloxy)pyridine

The title compound was obtained in the same manner as in Example 3b (yield: 47%) from the compound obtained in Example 12a.

Example 12c
2-(8-(2-Pyridyloxy)octylthio)benzimidazole (Compound 10)

The title compound was obtained in the same manner as in Example 3c (yield: 52%) by using the compound obtained in Example 12b and 2-mercaptobenzimidazole.

$^1$H-NMR (CDCl$_3$) (ppm): 1.31–1.50 (m, 8H), 1.77 (m, 4H), 3.34 (t, 2H), 4.26 (t, 2H), 6.74 (d, 1H), 6.87 (t, 1H), 7.20 (m, 2H), 7.51–7.58 (m, 3H), 8.17 (dd, 1H)

MS (FAB$^+$): m/z 356 (MH$^+$)

Example 13
Synthesis of 2-(5-(4-pyridyloxy)pentylthio)benzimidazole (Compound 19)

Example 13a
2-(5-Hydroxypentylthio)benzimidazole 1.5 g of 2-mercaptobenzimidazole and 1.7 g of 5-bromopentanol were refluxed for 5 hours in an acetonitrile solvent containing 1.2 g of triethylamine. The reaction mixture was cooled, then added with water and extracted with ethyl acetate. The extract was dried over sodium sulfate, and the solvent was evaporated under reduced pressure. The resulting residue was purified by silica gel column chromatography (ethyl acetate:hexane) to obtain 1.77 g of the title compound (yield: 75%).

Example 13b
2-(5-(4-Pyridyloxy)pentylthio)benzimidazole (Compound 19)

0.47 g of the compound obtained in Example 13a, 0.30 g of 4-bromo-pyridine, 0.80 g of KOH and 0.20 g of 18-crown-6-ether were added to 20 ml of dimethyl sulfoxide and heated to 150° C. for 8 hours. The reaction mixture was cooled, then added with water and extracted with ethyl acetate. The extract was dried over sodium sulfate, and the solvent was evaporated under reduced pressure. The resulting residue was purified by silica gel column chromatography (ethyl acetate) to obtain 0.19 g of the title compound (yield: 30%).

$^1$H-NMR (CDCl$_3$) (ppm): 1.60 (m, 2H), 1.82 (m, 4H), 3.36 (t, 2H), 3.94 (t, 2H), 6.79 (d, 2H), 7.20 (m, 2H), 7.52 (m, 2H), 8.17 (d, 2H)

MS (FAB$^+$): m/z 314 (MH$^+$)

Example 14
Synthesis of 2-(5-(2-benzimidazolylthio)pentyloxy)-1-isopropenyl-benzimidazole (Compound 20)

Example 14a
2-(5-Hydroxy-pentyloxy)-1-isopropenylbenzimidazole 3.3 g of 1,5-pentadiol and 0.4 g of sodium were stirred with heating for 30 minutes under nitrogen atmosphere. After the sodium disappeared, the reaction mixture was added dropwise with 30 ml of anhydrous THF containing 2.9 g of 2-chloro-1-isopropenylbenzimidazole and refluxed for 8 hours. The reaction mixture was cooled to room temperature, then added with water and extracted with ethyl acetate. The extract was dried over sodium sulfate, and the solvent was evaporated under reduced pressure. The resulting residue was purified by silica gel column chromatography (ethyl acetate) to obtain 2 g of the title compound (yield: 51%).

Example 14b
2-(5-Tosyloxy-pentyloxy)-1-isopropenylbenzimidazole

A solution of 2 g of the compound obtained in Example 14a in 20 ml of dichloromethane was added with 5 ml of pyridine and 1.8 g of p-toluenesulfonyl chloride and stirred for 5 hours. The organic layer was washed with 10% aqueous citric acid and then with water, and dried over anhydrous sodium sulfate. The solvent was evaporated under reduced pressure, and the resulting residue was purified by silica gel column chromatography (ethyl acetate:hexane) to obtain 2.2 g of the title compound (yield: 69%).

Example 14c
2-(5-(2-Benzimidazolylthio)pentyloxy)-1-isopropenylbenzimidazole (Compound 20)

0.415 g of the compound obtained in Example 14b and 0.15 g of 2-mercaptobenzimidazole were refluxed for 5 hours in 10 ml of acetonitrile solvent containing 0.15 g of triethylamine. After cooling to room temperature, the reaction mixture was added with water and extracted with ethyl acetate. The organic layer was dried over sodium sulfate, and the solvent was evaporated under reduced pressure. The obtained residue was purified by silica gel column chromatography (ethyl acetate:hexane) to obtain 0.28 g of the title compound (yield: 71%).

$^1$H-NMR (CDCl$_3$) (ppm): 1.59 (m, 2H), 1.88 (m, 4H), 3.34 (t, 2H), 4.56 (t, 2H), 5.22 (s, 1H), 5.35 (s, 1H), 7.19 (m, 4H), 7.26 (m, 1H), 7.52 (m, 2H)

MS (FAB$^-$): m/z 391 (M–H)

Example 15
Synthesis of 2-(5-(2-benzimidazolylthio)pentyloxy)benzimidazole (Compound 21)

Example 15a
2-(5-Tosyloxy-pentyloxy)benzimidazole 0.62 g of the compound obtained in Example 14b was dissolved in 10 ml of t-BuOH, added dropwise slowly with a mixed solution (30 ml) of 1.92 g of KMnO$_4$ and 50 ml of 0.1 N NaOH, and then the mixture was stirred for 1 hour. The reaction mixture was extracted three times with chloroform, and the organic layer was dried over sodium sulfate. The solvent was evaporated under reduced pressure, and the resulting residue was purified by silica gel column chromatography (ethyl acetate:hexane) to obtain 0.34 g of the title compound (yield: 61%).

Example 15b
2-(5-(2-Benzimidazolylthio)pentyloxy)benzimidazole (Compound 21)

188 mg of the compound obtained in Example 15a and 75 mg of 2-mercaptobenzimidazole were refluxed for 4 hours in 10 ml of acetonitrile containing 0.1 g of triethylamine. After cooling to room temperature, the reaction mixture was added with water and extracted with ethyl acetate. The extract was dried over sodium sulfate, and the solvent was evaporated under reduced pressure. The resulting residue was purified by silica gel column chromatography (ethyl acetate:hexane) to obtain 100m g of the title compound (yield: 57%).
$^1$H-NMR (CDCl$_3$) (ppm): 1.43 (m, 2H), 1.64 (m, 4H), 3.12 (t, 2H), 4.27 (t, 2H), 6.87 (m, 4H), 7.05–7.20 (m, 4H)
MS (FAB$^+$): m/z 353 (MH$^+$)

Example 16
Synthesis of 2-(5-(2-Pyridyloxy)hexyl)benzimidazole (Compound 22)

Example 16a
2-(6-Hydroxyhexyl)benzimidazole 1.6 g of methyl 7-hydroxyheptanoate and 1.08 g of o-phenylenediamine were refluxed for 7 hours in 15 ml of 2:1 hydrochloric acid aqueous solution. The reaction mixture was cooled to room temperature, then adjusted to pH 8 with addition of aqueous NaHCO$_3$ and extracted with ethyl acetate. The extract was dried over sodium sulfate, and the solvent was evaporated under reduced pressure. The resulting residue was purified by silica gel column chromatography (ethyl acetate) to obtain 0.9 g of the title compound (yield: 41%).

Example 16b
2-(5-(2-Pyridyloxy)hexyl)benzimidazole (Compound 22)

218 mg of the compound obtained in Example 16a, 115 mg of 2-chloropyridine, 200 mg of KOH and 50 mg of 18-crown-6-ether were added to 15 ml of DMSO and the mixture was heated to 150° C. for 8 hours. The reaction mixture was cooled, then added with water and extracted with ethyl acetate. The extract was dried over sodium sulfate, and the solvent was evaporated under reduced pressure. The resulting residue was purified by silica gel column chromatography (ethyl acetate) to obtain 150 mg of the title compound (yield: 51%).
$^1$H-NMR (CDCl$_3$) (ppm): 1.49 (m, 4H), 1.78 (m, 2H), 1.90 (m, 2H), 2.94 (t, 2H), 4.27 (t, 2H), 6.73 (d, 1H), 6.88 (t, 1H), 7.23 (m, 2H), 7.51–7.59 (m, 3H), 8.16 (dd, 1H)
MS (FAB$^+$): m/z 296 (MH$^+$)

Example 17
Synthesis of 2-(5-(2-benzothiazolylamino)pentylthio) benzimidazole

Example 17a
N-(5-Bromopentyl)phthalimide 3.7 g of 1,5-dibromopentane and 4.8 g of phthalimide potassium were stirred at 150° C. for 3 hours in 15 ml of DMF. After the DMF was evaporated under reduced pressure, the residue was added with water and ethyl acetate and separated. The organic layer was dried over sodium sulfate and the solvent was evaporated under reduced pressure. The resulting residue was purified by silica gel column chromatography (ethyl acetate) to obtain 4.5 g of the title compound (yield: 75%).

Example 17b
2-(5-(N-Phthalimide)pentylthio)benzimidazole 2.96 g of the compound obtained in Example 17a and 1.5 g of 2-mercaptobenzimidazole were refluxed for 5 hours in 20 ml of acetonitrile containing 1.2 g of triethylamine. The reaction mixture was cooled to room temperature, then added with water and extracted with ethyl acetate. The extract was dried over sodium sulfate, and the solvent was evaporated under reduced pressure. The resulting residue was purified by silica gel column chromatography (ethyl acetate:hexane) to obtain 2.96 g of the title compound (yield: 81%).

Example 17c
2-(5-Aminopentylthio)benzimidazole 1.82 g of the compound obtained in Example 17b and 0.85 g of hydrazine hydrate were refluxed for 5 hours in 25 ml of methanol. The reaction mixture was cooled to room temperature and then filtered. The filtrate was concentrated, washed with chloroform and concentrated again to obtain 1.1 g of the title compound (crude product).

Example 17d
2-(5-(2-Benzothiazolylamino)pentylthio)benzimidazole (Compound 30)

0.6 g of the compound obtained in Example 17c and 0.34 g of 2-chloro-benzothiazole were refluxed for 23 hours in 15 ml of isopropanol. The reaction mixture was cooled to room temperature, and the solvent was evaporated under reduced pressure. The resulting residue was purified by silica gel column chromatography (ethyl acetate:hexane) to obtain 0.32 g of the title compound (yield: 43%).
$^1$H-NMR (CDCl$_3$) (ppm): 1.59 (m, 2H), 1.70 (m, 2H), 1.82 (m, 2H), 3.33 (t, 2H), 3.43 (t, 2H), 7.04 (t, 1H), 7.15 (m, 2H), 7.24 (m, 1H), 7.47–7.60 (m, 4H)
MS (FAB$^-$): m/z 367 (M–H)

Example 18
Synthesis of 2-(5-(2-benzoxazolyl)pentylthioamino) benzimidazole (Compound 31)

0.6 g of the compound obtained Example 17c and 0.31 g of 2-chlorobenzoxazole were refluxed for 5 hours in 15 ml of isopropanol containing 0.21 g of triethylamine. After cooling to room temperature, the solvent was evaporated under reduced pressure. The resulting residue was purified by silica gel column chromatography (ethyl acetate:hexane) to obtain 0.34 g of the title compound (yield: 48%).
$^1$H-NMR (CDCl$_3$) (ppm): 1.58 (m, 2H), 1.73 (m, 2H), 1.82 (m, 2H), 3.31 (t, 2H), 3.41 (t, 2H), 6.97 (d, 1H), 7.12 (m, 3H), 7.27 (m, 2H), 7.47 (m, 2H)
MS (FAB$^+$): m/z 353 (MH$^+$)

Example 19
Synthesis of 2-(5-(5-chloro-2-benzoxazolylamino) pentylthio)-benzimidazole (Compound 33)

Example 19a
5-Chloro-2-(5-aminopentylthio)benzimidazole 1.5 g of the compound obtained in Example 17a and 0.93 g of 5-chloro-2-mercaptobenzimidazole were refluxed for 5 hours in 20 ml of acetonitrile containing 0.55 g of triethylamine. The reaction mixture was cooled to room temperature, then added with water and extracted with ethyl acetate. The extract was dried over sodium sulfate, and the solvent was evaporated under reduced pressure. The obtained residue was purified by silica gel column chromatography (ethyl acetate:hexane) to obtain 1.81 g of the title compound (yield: 91%). Subsequently, the product was added with 0.85 g of hydrazine hydrate and 25 ml of methanol and refluxed for 5 hours. The mixture was cooled to room temperature and then filtered. The filtrate was concentrated, washed with chloroform and then concentrated again to obtain 1 g of the title compound (crude product).

Example 19b
2-(5-(5-Chloro-2-benzoxazolylamino)pentylthio)benzimidazole (Compound 33)

0.6 g of the compound obtained in Example 19a and 0.31 g of 2-chlorobenzoxazole were refluxed for 5 hours in 15 ml of isopropanol containing 0.21 g of triethylamine. After cooling to room temperature, the solvent was evaporated under reduced pressure. The resulting residue was purified by silica gel column chromatography (ethyl acetate:hexane) to obtain 0.32 g of the title compound (yield: 41%).
$^1$H-NMR (CDCl$_3$) (ppm): 1.49 (m, 2H), 1.67 (m, 2H), 1.77 (m, 2H), 3.25 (t, 2H), 3.45 (t, 2H), 5.67 (br, 1H), 7.05 (t, 1H), 7.13 (m, 2H), 7.30 (m, 2H), 7.44 (m, 2H)
MS (FAB$^+$): m/z 387 (MH$^+$)

Example 20
Synthesis of 2-(5-(5-methyl-2-benzoxazolylamino)pentylthio)-benzimidazole (Exemplary Compound 34)

Example 20a
5-Methyl-2-(5-aminopentylthio)benzimidazole
The title compound was obtained in the same manner as in Example 19a (0.95 g, crude product) from 1.5 g of the compound obtained in Example 19a and 0.82 g of 5-methyl-2-mercaptobenzimidazole.

Example 20b
2-(5-(5-Methyl-2-benzoxazolylamino)pentylthio)benzimidazole (Exemplary Compound 34)
The title compound was obtained in the same manner as in Example 19b (0.33 g, yield: 45%) by using 0.6 g of the compound obtained in Example 20a and 0.31 g of 2-chlorobenzoxazole.
$^1$H-NMR (CD$_3$OD) (ppm): 1.58 (m, 2H), 1.70 (m, 2H), 1.77 (m, 2H), 2.41 (s, 3H), 3.23 (t, 2H), 3.36 (t, 2H), 7.00 (m, 2H), 7.12 (t, 1H), 7.23 (m, 2H), 7.45 (m, 1H)
MS (FAB$^+$): m/z 367 (MH$^+$)

Example 21
Synthesis of 2-(6-(2-benzoxazolylamino)hexylthio)benzimidazole (Exemplary Compound 32)

Example 21a
2-(6-Aminohexylthio)benzimidazole
The title compound was obtained in the manner described in Example 19a (yield: 46%) by treating a reaction product of 2-(6-bromohexylthio)benzimidazole and phthalimide potassium with hydrazine hydrate.

Example 21b
2-(6-(2-Benzoxazolylamino)hexylthio)benzimidazole (Exemplary Compound 32)
The title compound was obtained in the same manner as in Example 19b (yield: 37%) by using the compound obtained in Example 21a and 2-chlorobenzoxazole.
$^1$H-NMR (CD$_3$OD) (ppm): 1.40 (m, 4H), 1.66 (m, 2H), 1.76 (m, 2H), 3.26 (t, 2H), 3.36 (t, 2H), 6.99 (t, 1H), 7.15 (m, 3H), 7.24 (m, 2H), 7.43 (m, 2H)
MS (FAB$^-$): m/z 365 (M–H)

Example 22
Synthesis of 2-(2-(2-(2-benzoxazolylamino)ethoxy)ethylthio)-benzimidazole (Exemplary Compound 35)

Example 22a
2-(2-(2-Aminoethoxy)ethylthio)benzimidazole
The title compound was obtained in the manner described in Example 19a by treating a reaction product of 2-(2-(2-chloroethoxy)ethylthio)benzimidazole and phthalimide potassium with hydrazine hydrate.

Example 22b
2-(2-(2-(2-Benzoxazolylamino)ethoxy)ethylthio)benzimidazole (Exemplary Compound 35)
The title compound was obtained in the same manner as in Example 19b (yield: 22%) by using the compound obtained in Example 22a and 2-chlorobenzoxazole.
$^1$H-NMR (CDCl$_3$) (ppm): 3.45 (t, 2H), 3.70 (m, 4H), 3.81 (t, 2H), 6.12 (br, 1H), 7.05 (t, 1H), 7.16–7.25 (m, 4H), 7.38 (d, 1H), 7.51 (m, 2H)
MS (FAB$^+$): m/z 355 (MH$^+$)

Example 23
Synthesis of 2-(2-(2-(2-(2-benzoxazolylamino)ethoxy)ethoxy)ethylthio)-benzimidazole (Exemplary Compound 36)

Example 23a
2-(2-(2-(2-Aminoethoxy)ethoxy)ethylthio)benzimidazole
The title compound was obtained in the manner described in Example 19a by treating a reaction product of 2-(2-(2-(2-chloroethoxy)ethoxy)ethylthio)benzimidazole and phthalimide potassium with hydrazine hydrate.

Example 23b
2-(2-(2-(2-(2-Benzoxazolylamino)ethoxy)ethoxy)ethylthio)benzimidazole (Compound 36)
The title compound was obtained in the same manner as in Example 19b (yield: 36%) by using the compound obtained in Example 23a and 2-chlorobenzoxazole.
$^1$H-NMR (CDCl$_3$) (ppm): 3.57 (t, 2H), 3.69 (m, 6H), 3.76 (t, 2H), 3.86 (t, 2H), 6.16 (br, 1H), 7.07 (t, 1H), 7.19–7.30 (m, 4H), 7.42 (d, 1H), 7.53 (m, 2H)
MS (FAB$^+$): m/z 399 (MH$^+$)

Example 26
Synthesis of 2-(6-(4-pyridyloxy)hexylthio)benzimidazole (Compound 25)

Example 26a
2-(6-Hydroxyhexylthio)benzimidazole
3.0 g of 2-mercaptobenzimidazole and 3.8 g of 6-bromohexanol was added to 20 ml of isopropanol and refluxed with stirring for 5 hours. After cooling, the reaction mixture was neutralized with 2 N NaOH aqueous solution and extracted with ethyl acetate. The organic layer was washed with water and dried over sodium sulfate, and the solvent was evaporated under reduced pressure. The residue was purified by silica gel chromatography (20% ethyl acetate:methylene chloride) to obtain 5.0 g of the title compound (yield: 100%).

Example 26b
2-(6-(4-Pyridyloxy)hexylthio)benzimidazole (Compound 25)
0.5 g of the compound obtained in Example 26a, 0.4 g of 4-bromopyridine hydrochloride, 0.38 g of potassium hydroxide and 0.2 g of 18-crown-6-ether were added to 10 ml of DMSO and the mixture was heated to 150° C. with stirring for 6 hours. After cooling, the reaction mixture was added with water and extracted with ethyl acetate. The organic layer was washed with water and dried over sodium sulfate, and the solvent was evaporated under reduced pressure. The residue was purified by silica gel chromatography (ethyl acetate:methylene chloride=1:3) and crystallized from acetonitrile to obtain 0.14 g of the title compound (yield: 22%).

$^1$H-NMR (CDCl$_3$) (ppm): 1.50 (m, 4H), 1.78 (m, 4H), 3.36 (t, 2H), 3.99 (m, 6H), 6.79 (d, 2H), 7.20 (m, 2H), 7.50 (br, 2H), 8.42 (d, 2H)

MS (FAB$^+$): m/z 328 (MH$^+$)

The following compounds were synthesized in the same manner as in Example 26.

2-(8-Hydroxyoctylthio)benzimidazole, yield: 86% (Compound 26) Purified by silica gel chromatography (ethyl acetate:methylene chloride) and then crystallized from acetonitrile, yield: 48%.

$^1$H-NMR (CDCl$_3$) (ppm): 1.36 (m, 4H), 1.44 (m, 4H), 1.76 (m, 4H), 3.34 (t, 2H), 4.00 (m, 6H), 6.82 (d, 2H), 7.20 (m, 2H), 7.50 (br, 2H), 8.41 (d, 2H)

MS (FAB$^+$): m/z 356 (MH$^+$)

2-(4-Hydroxybutylthio)benzimidazole, yield: 59% (Compound 27) Purified by silica gel chromatography (ethyl acetate:methylene chloride), yield: 40%.

$^1$H-NMR (CDCl$_3$) (ppm): 1.98 (m, 4H), 3.40 (t, 2H), 4.03 (m, 6H), 6.79 (d, 2H), 7.20 (m, 2H), 7.50 (br, 2H), 8.41 (d, 2H)

MS (FAB$^+$): m/z 300 (MH$^+$)

Example 28

1-Methyl-2-(5-(2-pyridyloxy)pentylthio)benzimidazole (Compound 23)

0.2 g of (Compound 1) was dissolved in 1.2 ml of DMF, added with 0.27 g of potassium carbonate and 0.12 g of methyl iodide and the mixture was stirred at 50° C. for 1.5 hours. The reaction mixture was added with water and extracted with ethyl acetate. The organic layer was washed with water and dried over sodium sulfate, and the solvent was evaporated under reduced pressure. The residue was purified by silica gel chromatography (ethyl acetate:methylene chloride=1:6) to obtain 0.15 g of the title compound (yield: 72%).

$^1$H-NMR (CD$_3$OD) (ppm): 1.65 (m, 2H), 1.86 (m, 4H), 3.42 (t, 2H), 3.68 (s, 3H), 4.29 (t, 2H), 6.71 (d, 2H), 6.84 (ddd, 1H), 7.21 (m, 2H), 7.55 (ddd, 1H), 7.67 (m, 1H), 8.13 (ddd, 1H)

MS (FAB$^+$): m/z 328 (MH$^+$)

Example 29

1-Propionyl-2-(5-(2-pyridyloxy)pentylthio)benzimidazole (Compound 24)

0.2 g of (Compound 1) was dissolved in 0.8 ml of dimethylacetamide and 1.6 ml of acetonitrile, added with 0.14 ml of triethylamine and then added with 74 mg of propionyl chloride at 50° C. After 30 minutes, the reaction mixture was cooled and added with water and extracted with ethyl acetate. The organic layer was washed with water and dried over sodium sulfate, and the solvent was evaporated under reduced pressure. The residue was purified by using a silica gel column (ethyl acetate:methylene chloride=1:5) and crystallized from ethyl acetate:hexane to obtain 0.17 g of the title compound (yield: 72%).

$^1$H-NMR (CD$_3$OD) (ppm): 1.38 (t, 3H), 1.69 (m, 2H), 1.88 (m, 4H), 3.09 (t, 2H), 3.37 (t, 2H), 4.31 (q, 2H), 6.72 (d, 1H), 6.84 (ddd, 1H), 7.28 (m, 2H), 7.55 (ddd, 1H), 7.63 (d, 1H), 7.79 (d, 1H), 8.13 (dd, 1H)

MS (FAB$^+$): m/z 370 (MH$^+$)

Example 30

Synthesis of 1-methoxymethyl-2-(5-(N-(2-pyrazyl)amino) pentylthio)-benzimidazole (Compound 28)

Example 30a

Synthesis of 5-(2-benzimidazoylthio)pentyl bromide 6.0 g of 2-mercaptobenzimidazole and 60 g of 1,5-dibromopentane were dissolved in 50 ml of ethanol and the mixture was refluxed under heating for 6 hours. After the solvent was evaporated under reduced pressure, the residue was digested with 50 ml of ethyl acetate and 50 ml of hexane to obtain about 12 g of solid. The solid was added with 100 ml of water and neutralized with aqueous sodium hydroxide. The deposited oil-soluble substance was extracted with ethyl acetate, washed with water and then concentrated. The residue was purified by silica gel column chromatography (chloroform) to obtain 8.7 g of crude crystals. The crystals were recrystallized from ethanol to obtain 7.8 g of the target title compound (yield: 66%).

Melting point: 126–127° C.

MS (FAB$^+$): m/z 300 (MH$^+$)

Example 30b

1-Methoxymethyl-2-(5-bromopentylthio)benzimidazole 2.99 g of the compound obtained in Example 30a and 6.46 g of diisopropylethylamine were added to 20 ml of dimethylformamide and cooled on ice. The reaction mixture was added with 1.93 g of chloromethyl ether and reacted overnight at room temperature. The reaction mixture was poured into water and extracted with 200 ml of ethyl acetate, and the organic layer was washed with water and saturated brine and dried over sodium sulfate. After the solvent was evaporated under reduced pressure, the residue was purified by silica gel column chromatography (hexane:ethyl acetate=3:1) to obtain 2.0 g of the title compound as pale yellow oil (yield: 58%).

Example 30c

1-Methoxymethyl-2-(5-(2-pyrazylamino)pentylthio) benzimidazole (Compound 28)

0.69 g of the compound obtained in Example 31b and 0.19 g of 2-aminopyrazine were added to 3 ml of 1,3-dimethyl-2-imidazolidinone, added with 96 mg of sodium hydride and the mixture was reacted at 60° C. for 30 minutes. The reaction mixture was poured into water and extracted with ethyl acetate, and the organic layer was washed with 50 ml of water and saturated brine and dried over sodium sulfate. After the solvent was evaporated under reduced pressure, the residue was purified by silica gel column chromatography (hexane:ethyl acetate=2:1) to obtain 0.34 g of the title compound as pale yellow oil (yield: 48%).

$^1$H-NMR (CDCl$_3$): (ppm): 1.55 (m, 2H), 1.70 (m, 2H), 1.86 (q, 2H), 3.32 (s, 3H), 3.40 (m, 4H), 5.45 (s, 2H), 7.23 (m, 2H), 7.40 (m, 1H), 7.66 (m, 1H), 7.75 (d, 2H), 7.84 (brs, 1H), 7.94 (m, 1H)

MS (FAB$^+$): m/z 358 (MH$^+$)

Example 31

Synthesis of 2-(5-(3-(1,2,4-triazyl)amino)pentylthio) benzimidazole (Compound 29)

Example 31b 1-(2-Trimethylsilylethoxy)methyl-2-(5-bromopentylthio) benzimidazole 1.5 g of the compound obtained in Example 30a and 3.23 g of diisopropyl-ethylamine was added to 10 ml of dimethylformamide and cooled on ice. The reaction mixture was added with 1.67 g of 2-trimethylsilylethoxymethyl chloride, and reacted overnight at room temperature, and then poured into water. The mixture was extracted with ethyl acetate. The organic layer was washed with saturated brine and dried over sodium sulfate. After the solvent was evaporated under reduced pressure, the residue was purified by silica gel column chromatography (hexane:ethyl acetate=10:1 to 4:1) to obtain 1.84 g of the title compound as colorless oil (yield: 86%).

Example 31c 1-(2-Trimethylsilylethoxy)methyl-2-(5-(3-(1,2,4-triazylamino)-pentylthio)benzimidazole 96 mg of 3-amino-1,2,4-triazine and 430 mg of the compound obtained in Example 32b were added to 2 ml of 1,3-dimethyl-2-imidazolidinone, further added with 48 mg of sodium hydride, and then the mixture was reacted at room temperature for 3 hours The reaction mixture was poured into water and extracted with ethyl acetate. The ethyl acetate layer was washed with water and saturated brine and dried over sodium sulfate. After the solvent was evaporated under reduced pressure, the residue was purified by silica gel column chromatography (hexane:ethyl acetate=2:1 to ethyl acetate) to obtain 135 mg of the title compound as pale yellow oil (yield: 30%).

Example 31d 2-(5-(3-(1,2,4-Triazyl)amino)pentylthio)benzimidazole (Compound 29)

35 mg of the compound obtained in Example 31c and 0.8 ml of 1 M tetra-n-butylammonium chloride were added to 1 ml of hexamethylphosphoramide and the mixture was reacted at 50° C. for 5 hours. The reaction mixture was poured into water and extracted with ethyl acetate. The ethyl acetate layer was washed with water and saturated brine and dried over sodium sulfate. After the solvent was evaporated under reduced pressure, the residue was purified by silica gel column chromatography (ethyl acetate) to obtain 15 mg of the title compound as pale yellow oil (yield: 60%).
$^1$H-NMR (CDCl$_3$+CD$_3$OD): (ppm): 1.49 (m, 2H), 1.63 (m, 2H), 1.79 (q, 2H), 3.28 (t, 2H), 3.46 (m, 2H), 7.19 (m, 2H), 7.48 (br, 2H), 8.12 (d, 1H), 8.48 (d, 1H)
MS (FAB$^+$): m/z 315 (MH$^+$)

Test Example 1

Activity of the compounds of the present invention for suppressing the foaming of macrophages, which triggers arterial sclerosis, was examined.
(1) In vitro experiment using mouse peritoneal macrophages, 15-Week old female ICR mice (Nippon SLC) were subjected to bleeding by cutting off their cervicalis, and Hanks buffer (Nippon Seiyaku) was injected into their peritoneal cavities. After abdominal regions of the mice were massaged, the buffer was recovered immediately, and then the resulting buffer was centrifuged at 1,000 r.p.m. for five minutes to collect peritoneal macrophages. Then, the collected macrophages were suspended in GTI medium (Wako Pure Chemical Industries), and inoculated onto a 24-well microtiter plate. After the macrophages were cultivated at 37° C. under 5% CO$_2$ for two hours, the culture medium was changed with Dulbecco Modified Eagle Medium (MEM, Nippon Seiyaku). The macrophages were further cultivated at 37° C. under 5% CO$_2$ for 16 hours, and then a test compound and liposomes were added to the culture.
1) Test compound: dissolved in DMSO (Wako Pure Chemical Industries), 2) Liposomes: PC/PS/DCP/CHOL=50/50/10/75 (nmol)
  PC: Phosphatidylcholine (Funakoshi);
  PS: Phosphatidylserine (Funakoshi);
  DCP: Dicetylphosphate (Funakoshi);
  CHOL: Cholesterol (Sigma)

After cultivation was further continued at 37° C. under 5% CO$_2$ for 16 hours, lipid fraction was extracted with chloroform and methanol. The extracted lipid fraction was dissolved in isopropyl alcohol, and the produced cholesterol ester (CE) was quantified by an enzymatic luminescence method. Yield of the cholesterol ester was calculated as a relative ratio based on yield of the control as 100% where no test compound was added.

| Compound | Dose | CE yield (%) |
| --- | --- | --- |
| (1) | 5 µM | 4.1 |
| (2) | 5 µM | 21 |
| (3) | 5 µM | 18 |
| (4) | 5 µM | 20 |
| (5) | 5 µM | 11 |
| (6) | 5 µM | 12 |
| (7) | 5 µM | 14 |
| (8) | 5 µM | 17 |
| (9) | 5 µM | 6.2 |
| (10) | 5 µM | 12 |
| (11) | 5 µM | 18 |
| (12) | 5 µM | 13 |
| (13) | 5 µM | 20 |
| (14) | 5 µM | 21 |
| (15) | 5 µM | 18 |
| (16) | 5 µM | 14 |
| (17) | 5 µM | 14 |
| (18) | 5 µM | 19 |
| (19) | 5 µM | 4.2 |
| (20) | 5 µM | 22 |
| (21) | 5 µM | 18 |
| (22) | 5 µM | 18 |
| (23) | 5 µM | 21 |
| (24) | 5 µM | 25 |
| (25) | 5 µM | 2.8 |
| (26) | 5 µM | 19 |
| (27) | 5 µM | 12 |
| (28) | 5 µM | 24 |
| (29) | 5 µM | 12 |
| (30) | 5 µM | 4.2 |
| (31) | 5 µM | 4.1 |
| (32) | 5 µM | 12 |
| (33) | 5 µM | 11 |
| (34) | 5 µM | 3.2 |
| (35) | 5 µM | 9.7 |
| (36) | 5 µM | 12 |
| (Ref. 1) | 5 µM | 78 |
| (Ref. 2) | 5 µM | 95 |
| (Ref. 3) | 5 µM | 10 |
| (Ref. 4) | 5 µM | 11 |
| (Ref. 5) | 5 µM | 14 |
| (Ref. 6) | 5 µM | 42 |

(Ref. 1) Compound (3) described in Bio. Med. Chem. Lett., Vol. 5 (2), 167–172 (1995)
(Ref. 2) Compound (9) described in WO98/54153
(Ref. 3) Compound (B30) described in EP849259
(Ref. 4) Compound (B49) described in EP849259
(Ref. 5) Compound (B12) described in EP849259
(Ref. 6) Compound (115) described in WO99/25712

From these results, it is clearly understood that the compounds of the present invention acted on macrophases and remarkably reduced the rate of cholesterol ester synthesis (a smaller value means a more potent suppression, and 100% indicates no suppression). The known benzimidazole derivatives used for comparison, i.e., Compounds of (Ref. 1) and (Ref. 2), had a benzimidazole structure relatively similar to that of the compounds of the present invention, however, they exerted almost no inhibitory effect on macrophages. Whilst, Compounds of (Ref. 3), (Ref. 4) and (Ref. 5)

inhibited the foaming of macrophages. Further, Compound of (Ref. 6) was moderate and not potent in suppression of foaming of macrophages.

Test Example 2

The compounds of the present invention were orally administered to mice to evaluate AUC (area under the plasma concentration).

8-week old BALB/cA male mice (Charles River Japan) were conditioned for one week after arrival and then used. Each test substance was dispersed in a medium containing 10% macrogol (Yoshida Seiyaku) and 90% physiological saline (Hikari Seiyaku) to prepare 5 mg/ml test substance suspension. Each prepared suspension was orally administered to 6 mice (30 mg/kg) at the same time, and cervical spine of one mouse was dislocated at each time, i.e., immediately after the administration, and 30 minutes, 1 hour, 2 hours, 4 hours and 6 hours after the administration. The whole blood was collected from abdominal aorta and blood level of the test substance was determined by liquid chromatography. The unit of AUC calculated from these results was µg/ml.hr.

| Compound | AUC | Compound | AUC |
|---|---|---|---|
| (1) | 0.34 | (2) | 1.22 |
| (3) | 0.84 | (4) | 0.26 |
| (5) | 0.10 | (6) | 0.68 |
| (7) | 0.18 | (8) | 0.31 |
| (9) | 0.11 | (11) | 0.24 |
| (13) | 0.15 | (15) | 0.68 |
| (16) | 1.41 | (17) | 1.22 |
| (19) | 5.52 | (21) | 2.42 |
| (22) | 1.26 | (23) | 0.86 |
| (25) | 1.21 | (26) | 0.15 |
| (27) | 0.43 | (28) | 0.41 |
| (29) | 0.18 | (30) | 0.23 |
| (31) | 0.24 | (33) | 1.23 |
| (34) | 0.85 | (36) | 0.68 |
| (Ref. 3) | 0.00 | (Ref. 4) | 0.00 |
| (Ref. 5) | 0.00 | | |

From these results, it can be understood that the compounds of the present invention were readily uptaken into blood (0.1 or more of AUC is preferred for exerting efficacy by oral administration, and 1 or more of AUC is more preferred for reliable exertion of efficacy, and when the value is 1 or more, extremely high effectiveness can be obtained by oral administration even if fluctuation due to difference of animal species is taken into consideration). Whilst, Compounds of (Ref.3), (Ref.4) and (Ref.5) were not uptaken into blood stream. It can be understood that, although these compounds are possibly suppress the foaming of macrophages in vitro, their efficacy by oral administration cannot be expected.

Test Example 3

Inhibitory activity of the compounds of the present invention against ACAT was evaluated.

Microsomes were prepared in a conventional manner from thorax aorta of a rabbit fed for 8 weeks with 1% cholesterol feed, and then suspended in 0.15 M phosphate buffer (pH 7.4) to prepare an enzyme solution. Measurement of inhibitory activity against ACAT was performed according to the method of J. G. Heider (J. Lipid Res., 24, 1127–1134 (1983)). 2 µl of test compound dissolved in dimethyl sulfoxide was added to 88 µl of 0.15 M phosphate buffer (pH 7.4) containing $^{14}$C-Oleyl-CoA(40 µM, 60000 dpm) and bovine serum albumin (2.4 mg/ml), and the mixture was incubated at 37° C. for 5 minutes. The mixed solution was added with 10 µl of the enzyme solution, and the mixture was reacted at 37° C. for 5 minutes and added with 3 ml of chloroform/methanol (2/1) and 0.5 ml of 0.04 N hydrochloric acid to terminate the reaction. Then, lipid was extracted. The solvent layer was concentrated to dryness, then dissolved in hexane, spotted on a TLC plate (Merck) and developed with hexane/ether/acetic acid (75:25:1). Radioactivity of the produced cholesterol ester fraction was measured by using BAS 2000 (Fuji Photo Film), and IC$_{50}$ value was calculated by comparison relative to a control in which only dimethyl sulfoxide was added.

| Compound | ACAT derived from vessel IC$_{50}$(µM) |
|---|---|
| (1) | 8.2 |
| (5) | 6.7 |
| (6) | 7.2 |
| (9) | 5.1 |
| (10) | 8.6 |
| (19) | 6.8 |
| (25) | 7.9 |
| (30) | 4.7 |
| (31) | 4.3 |
| (34) | 4.8 |
| (35) | 4.2 |
| (Ref. 6) | 0.021 |

From these results, it can be understood that the inhibitory activity against ACAT of the compounds of the present invention was significantly weak, and they suppress the foaming of macrophages independently from ACAT activity. Whilst, Compound of (Ref.6) was potent in ACAT inhibitory activity, and side effects due to the ACAT inhibition is strongly concerned.

Industrial Applicability

The benzimidazole derivatives of the present invention have an action of suppressing the foaming of macrophages, and they have excellent oral absorbability. Accordingly, they are useful as active ingredients of medicaments for preventive and/or therapeutic treatment of arteriosclerosis or medicaments for preventive and/or therapeutic treatment of hyperlipidemia. Further, they are also useful as additives for silver halide photosensitive materials or for the production of liquid crystals.

What is claimed is:

1. A benzimidazole compound represented by the following formula (I) or a salt thereof:

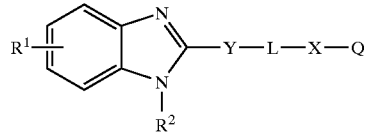

wherein, $R_1$ represents one or more functional groups on the benzene ring selected from the group consisting of hydrogen atom, a halogen atom, a lower alkyl group, and a lower alkoxy group; $R_2$ represents hydrogen atom, an alkyl group, or an acyl group; L represents a $C_4$–$C_8$ alkylene group, or an ethyleneoxy bridging group represented as $(CH_2CH_2O)_n$ $CH_2CH_2$ wherein n represents 1 or 2; X represents O or NH wherein NH may have a functional group on the nitrogen atom; Y represents S or a single bond; Q is a residue of a heterocyclic ring selected from the group consisting of pyridine, pyrimidine, pyrazine, triazine, pyrrole, thiophene, furan, imidazole, pyrazole, triazole, tetrazole, thiazole, thiadiazole, oxazole, oxadiazole, benzimidazole, benzoxazole, and benzothiazole; and X binds to a carbon atom contained in Q.

2. The compound or a salt thereof according to claim 1, wherein Y is S.

3. The compound or a salt thereof according to claim 1 or 2, wherein $R^1$ and $R^2$ represent hydrogen atom.

4. The compound or a salt thereof according to any one of claim 1 or 2, wherein L is a $C_4$–$C_8$ alkylene group.

5. The compound or a salt thereof according to claim 1, wherein Q is a residue of a heterocyclic ring selected from the group consisting of pyridine, thiazole, benzimidazole, benzoxazole and benzothiazole.

6. The compound or a salt thereof according to claim 1, wherein X is O.

7. A medicament comprising the compound according to claim 1 or a physiologically acceptable salt thereof as an active ingredient and a pharmaceutical additive.

8. The medicament according to claim 7, which is used for preventive or therapeutic treatment of hyperlipidemia.

9. The medicament according to claim 7, which is used for preventive or therapeutic treatment of arteriosclerosis.

10. The medicament according to claim 7, which is used as an agent for suppressing foaming of a macrophage.

11. The medicament according to claim 7, which is used as an agent for retracting arterial sclerosis lesions.

12. The medicament according to claim 7, which is used as an agent for inhibiting formation of arterial sclerosis lesions.

13. A method for preventive or therapeutic treatment of arteriosclerosis, which comprises the step of administering a preventively or therapeutically effective amount of the compound according to claim 1 or a physiologically acceptable salt thereof to a mammal.

14. The method according to claim 13, wherein said mammal is a human.

* * * * *